United States Patent [19]

Picha et al.

[11] Patent Number: 5,007,900
[45] Date of Patent: Apr. 16, 1991

[54] PERCUTANEOUS ENDOSCOPIC GASTROSTOMY DEVICE

[75] Inventors: George J. Picha, Independence; Dean J. Secrest, Euclid, both of Ohio

[73] Assignee: Applied Medical Technology, Inc., Independence, Ohio

[21] Appl. No.: 429,769

[22] Filed: Oct. 31, 1989

[51] Int. Cl.⁵ ............................................... A61M 5/32
[52] U.S. Cl. ................................... 604/106; 604/175; 604/178; 604/247
[58] Field of Search .................. 604/106, 107, 93, 174, 604/175, 178, 247, 256, 271, 280

[56] References Cited

U.S. PATENT DOCUMENTS

| | | | |
|---|---|---|---|
| 4,311,148 | 1/1982 | Courtney | 604/175 |
| 4,393,873 | 7/1983 | Nawash et al. | 604/174 |
| 4,573,576 | 3/1986 | Krol | 604/29 |
| 4,666,433 | 5/1987 | Parks | 604/178 |
| 4,668,225 | 5/1987 | Russo et al. | 604/270 |
| 4,863,438 | 9/1989 | Gauderer et al. | 604/175 |

Primary Examiner—Phen C. Pellegrino
Assistant Examiner—Ralph A. Lewis
Attorney, Agent, or Firm—Pearne, Gordon, McCoy & Granger

[57] ABSTRACT

A gastrostomy device that may be placed either endoscopically or percutaneously is disclosed. The catheter is a resilient tube with a resilient T-bar at one end. One wing of the T is provided with a pocket for the tip of an obturator rod. By inserting the rod in the pocket and orienting the rod along the tube, the bar is forced to a position in-line with the tube. The catheter may then be easily inserted into an established stoma. When the rod is removed, the bar returns to its orthogonal position, thereby retaining the catheter within the stomach. The device may be provided with a cup-shaped bolster whose mouth engages the skin about, but not adjacent to, the stoma to hold the bar snugly against the stomach wall. By providing the bolster with air vents, healing of the stoma is encouraged. By providing the device with two diametrically opposed pockets in the T-bar, a forked obturator may be used to fold both wings into a forward oriented, small axial cross section configuration for insertion into a stoma.

25 Claims, 4 Drawing Sheets

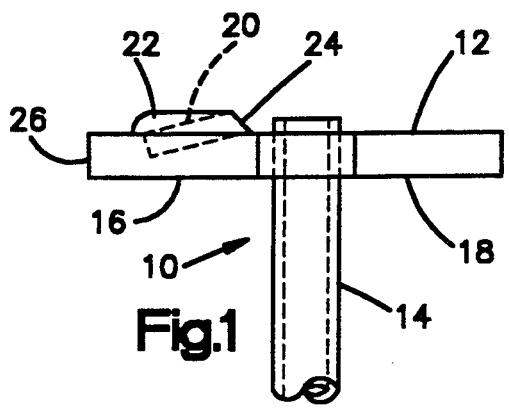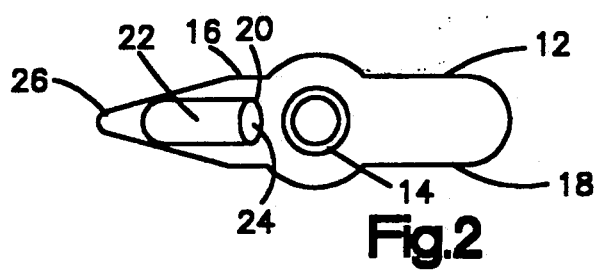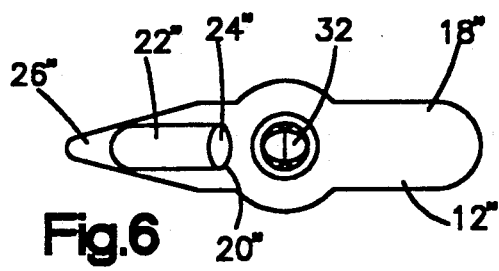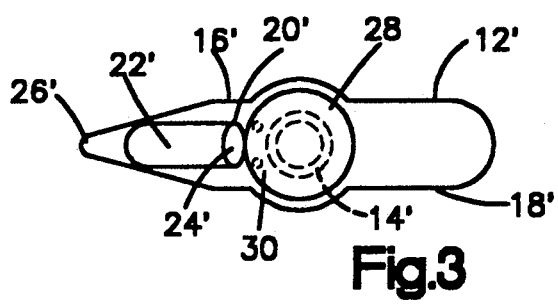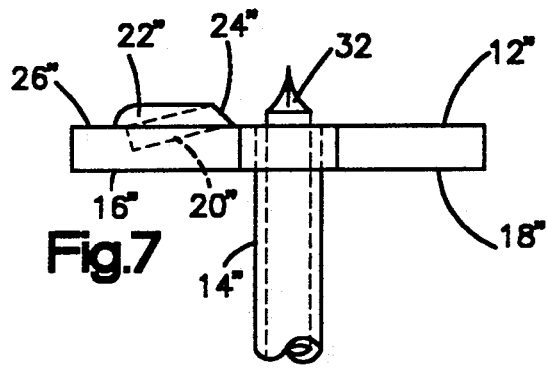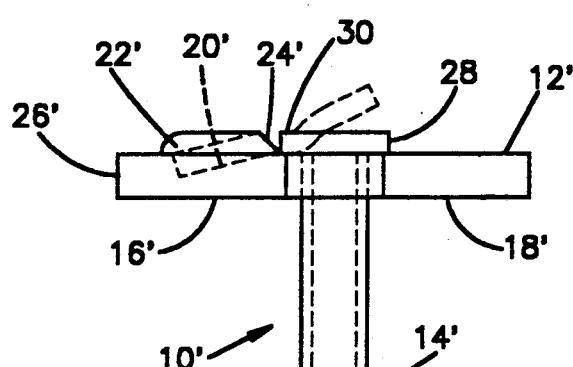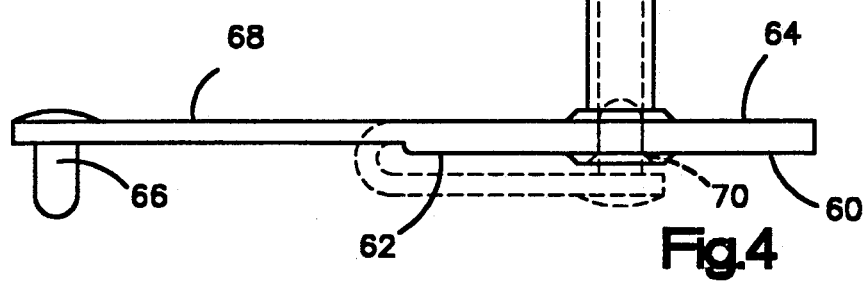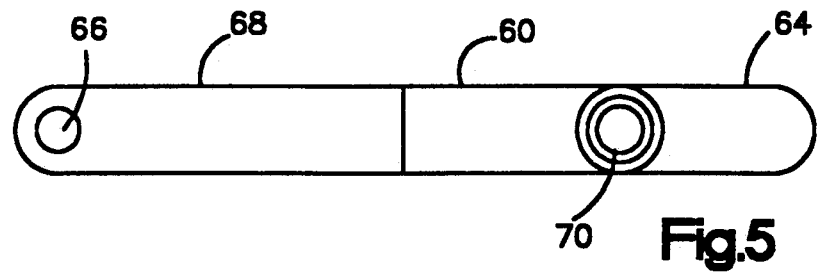

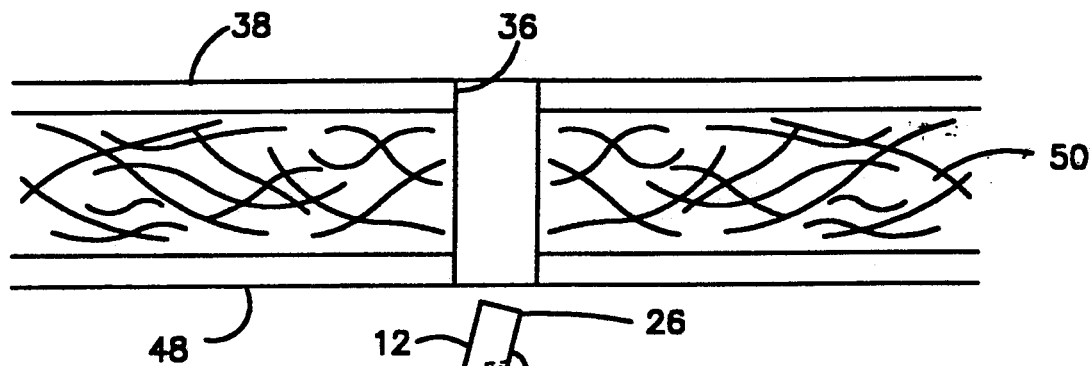
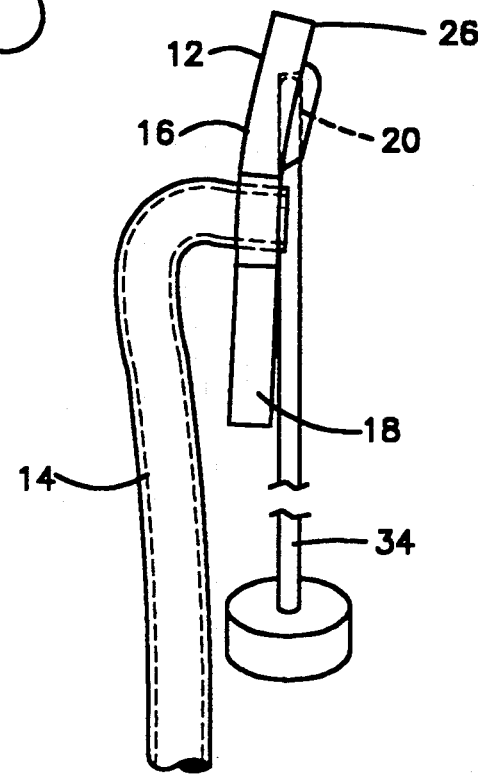
Fig.8
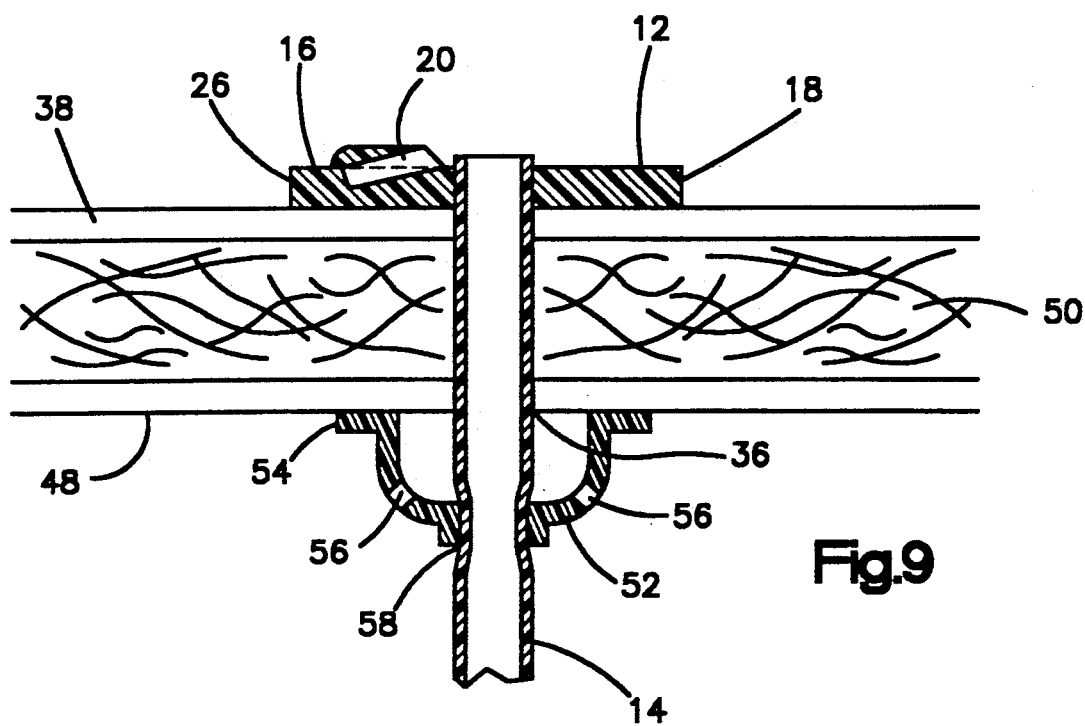
Fig.9

PERCUTANEOUS ENDOSCOPIC GASTROSTOMY DEVICE

BACKGROUND OF THE INVENTION

The invention relates to a gastrostomy device which is designed to be inserted through an opening in the wall of the abdomen and stomach of a patient for use in supplying nutrients and other fluids, including medication, into the stomach. Also, such a device can be used for decompression, and provides access for examination endoscopically, for example, using fiber optics. Other uses requiring insertion of a tube into other viscera for the body may be made of the device, such as bladder drainage, illeostomy, jejunostomy, colostomy, and cystostomy.

Certain medical conditions require the long term access for such purposes as internal feedings and/or medication to a person's stomach or other viscera of the body. This may be accomplished by inserting a tube through a surgical opening into the stomach or other viscera. Various devices have been used for this purpose.

U.S. Pat. Nos. 4,311,148 and 4,668,225 show feeding tubes or catheters having resilient wing-like protrusions about the end of the tube for retaining the tubes within a passage through the wall of a body cavity. The tubes are designed to be inserted into the patient through fresh incisions that are then sutured about the tube. To remove these tubes from the cavity it is possible to pull the end through the passage while exerting sufficient force to fold the wings back out of the way.

U.S. Pat. No. 4,573,576 shows a catheter with a disk-like retainer on one end. A line is introduced through an incision in the patient's skin, fascia and stomach wall and an endoscope used to capture the loose end within the stomach and to draw it out the patients's mouth. The line is then used to draw the tube portion of the catheter out through the incision. An endoscope is also used to remove the catheter.

After an incision establishes a passage through the body wall and a tube is passed therethrough, over a period of time the body heals to a degree about the tube. The passage or stoma becomes relatively stable, much like the hole for pierced ears for example. Without the tube it would eventually close up, but in the meantime, a well-defined passage exists even if the tube is withdrawn.

This well-defined passage is suitable for the external percutaneous insertion of appropriately designed catheters. However, none of the aforementioned devices are suitable for this purpose largely because of the difficulty in pushing a flexible tube versus pulling it and also because the folded-over wings make a poor dilator for the passage.

U.S. Pat. No. 4,863,438 which is included herein in its entirety by reference, shows a catheter that may be inserted into the stoma from outside the body. A hollow mushroom-shaped resilient head on the tube may be distended by the insertion of a rigid obturator into the tube, the distended head acting as a dilator small enough to pass through the stoma. Once the head clears the stoma, the obturator is withdrawn and the head expands. A similar process is employed to remove this device, or mechanical traction may be used to remove the device.

While unlike the other devices, this device may be inserted into an established stoma from outside the body, it is relatively difficult and expensive to manufacture because the head of the device is hollow. This necessitates either at least a two-piece construction or a much more expensive molding process.

SUMMARY OF THE INVENTION

The present invention is directed to a catheter that may be placed either endoscopically or percutaneously. In addition, it is simpler and less expensive to manufacture than prior art percutaneous gastrostomy devices.

The catheter comprises a resilient tube having a distal end and a proximal end, the distal end having a resilient retainer connected about it. The retainer means is provided with a pocket spaced radially outward from the tube.

The tube and retainer may, for example, be made of silicone rubber.

The pocket is adapted to receive the tip of a rod, whereby the retainer may be urged to a position collateral with the tube by inserting the tip in the pocket and orienting the rod collateral with the tube.

In the preferred embodiment, the retainer is a pair of diametrically spaced, oppositely extended wings, one of which contains the pocket.

In addition, it is preferred that the wing bearing the pocket taper to a point. This point then serves to help dilate the passage.

In another embodiment, the catheter may additionally be provieed with a one-way valve connected at the distal end. This valve prevents the reflux of the contents of the stomach or other cavity into the catheter. This valve may, for example, be a flapper valve or a duck-bill valve.

To seal against the stomach or other wall, it is important that the retainer bear against the wall. This may be done by trapping the wall/passage between the retainer and some form of projection from the tube on the external portion.

In one of the preferred embodiments, a resilient flange is connected about the proximal end, the axial distance between the retainer and the flange substantially corresponding to the length of the passage. This correspondence then keeps both the flange and the retainer snug against the wall.

In the preferred embodiment, the flange is a pair of diametrically spaced, oppositely extending, substantially flat wings.

A removable plug may be advantageously connected to the radially outer end of one of the flange wings by a flexible membrane which permits the plug to be inserted into the proximal end of the tube to close it off.

In another of the preferred embodiments, the retainer is held snugly against the wall by a new and improved bolster.

The bolster comprises a cup-shaped resilient member with a central aperture and one or more vent holes.

The aperture is expanded to slide over the proximal end of the tube and along the tube until the mouth engages the wall, when the aperture is allowed to contract, it firmly grips the tube.

Because the mouth of the cup engages the wall (i.e. skin), the area of the skin near the tube is open to air that can enter through the vent hole(s). This promotes healing of the stoma and helps prevent irritation and infection.

By providing the invention with two diametrically opposed pockets, an alternate means of installation may be provided. The prongs of a forked obturator are each inserted in a pocket, thereby holding the retaining means in a folded-forward configuration that provides a small axial cross section to facilitate insertion into a stoma.

BRIEF DESCRIPTION OF THE DRAWINGS

FIG. 1 is a side elevation view of a catheter according to the invention.

FIG. 2 is a top plan view of a catheter according to the invention.

FIG. 3 is a top plan view of an additional embodiment of the invention.

FIG. 4 is a side elevation view of the embodiment of FIG. 3.

FIG. 5 is a bottom plan view of the embodiment of FIG. 3.

FIG. 6 is a top plan view of still another embodiment of the invention.

FIG. 7 is a side elevation view of the embodiment shown in FIG. 6.

FIG. 8 is a perspective view of the catheter according to the invention being inserted into a passage or stoma.

FIG. 9 is a cross sectional side elevation view of the catheter according to the invention installed in a stoma and retained with a bolster according to one aspect of the invention.

DETAILED DESCRIPTION OF THE PREFERRED EMBODIMENTS

Figure 10:
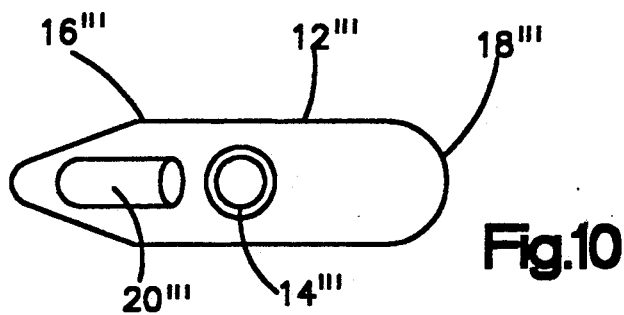
FIG. 10 is a top plan view of yet another embodiment of the invention.

Referring to FIGS. 1 and 2, a portion of a catheter 10 according to the invention is shown. The catheter 10 may be formed of any resilient material suitable for extended use in contact with body fluids, for example, silicone rubber.

A retainer 12 is attached about one end of a tube 14. The retainer 12 must everywhere be radially wider than the outside diameter of the tube 14 in order to provide a circumferential area about the tube 14 to sealingly bear against the stomach or other bodily wall. The retainer 12 may be formed integrally with the tube 14 or attached about the tube 14 by such methods as gluing.

The tube 14 may in general be of any desired length. While the size of the tube may in general also be a matter of choice, it has been found that sizes of 15, 20 and 24 French present adequate choices for most situations.

The retainer 12 may be advantageously in the form of two diametrically opposed generally flat wings 16 and 18. The wing 16 is provided with a pocket 20, the top wall 22 of which protrudes above the general level of the wing 16. The mouth 24 of the pocket 20 is located toward the tube 14 on the top of the wing 16, while the pocket 20 extends within the wing 16 radially outward from the tube 14. The wings may, for example, be approximately ⅛ inch thick and 1½ inches tipt-to-tip.

It would of course be possible to have the mouth of the pocket on the bottom of a wing.

In the preferred embodiments, the pocket-bearing wing 16 tapers to a point 26.

If desired, the retainer 12 may be provided with a one-way valve to prevent the reflux of fluids into the tube from, for example, the stomach.

FIGS. 3 and 4 show a retainer 12' provided with a flapper valve 28. The valve 28 consists of a resilient disk coaxially bonded at one edge 30 to the retainer 12'. The valve flexes away from the retainer 12' when fluid exits the retainer end of the tube 14', but seals against the retainer 12' when fluid attempts to enter the tube 14'.

As an alternative embodiment, FIGS. 6 and 7 show a retainer 12" provided with a duck-bill valve 32 at the retainer end of the tube 14".

Referring to FIGS. 8 and 9, the catheter 10 may be installed percutaneously.

The tip of an obturator or rod 34 inserted in the pocket 20 and the rod oriented collaterally back along the tube 14. The retainer 12 is urged to follow the orientation of the rod 34, forcing the tube 14 to flex. The retainer 12 is thereby held collateral with the rod 34 and the tube 14.

The rod 14 and the retainer 12 are then inserted into a stoma 36. The point 26 on the retainer 12 provides for ready dilation of the stoma 36, particularly if a surgical lubricant is applied to the catheter 10.

Once the entire retainer 12 is through the stoma 36, the rod 14 may be withdrawn leaving the retainer 12 behind and allowing the retainer 12 to return to its normal position as shown in FIG. 9, thus retaining the tube 14 within the stoma 36.

If desired, the catheter 10 may be removed from the stoma 36 by pulling on the tube 14 to pull the retainer 12 through the stoma 36, the wings 16 and 18 folding back out of the way.

The size of the wings 16 and 18 determine the amount of force required to remove the catheter 10. For easier removal, the wings 16 and 18 may widen to encircle the tube 14 as shown in the embodiment of FIG. 2. For more difficult removal, the wings 16''' and 18''' may be generally of constant width as shown in the embodiment of FIG. 10.

In addition, the catheter 12 may be installed endoscopically as decribed in the background of the invention. In this way, the catheter of the invention allows a single type catheter to be used for either endoscopic placement or percutaneous placement in an established stoma.

To insure a seal between the inner wall 38 about the stoma 36 and the retainer 12, it is necessary that the retainer 12 be urged against the wall 38 by applying some tension on the outer end of the tube 14. This may be done by placing a bolster over the tube 14 at the outer wall 48 about the stoma 36 such that the wall 50 is slightly compressed between the bolster and the retainer 12.

Figure 11:
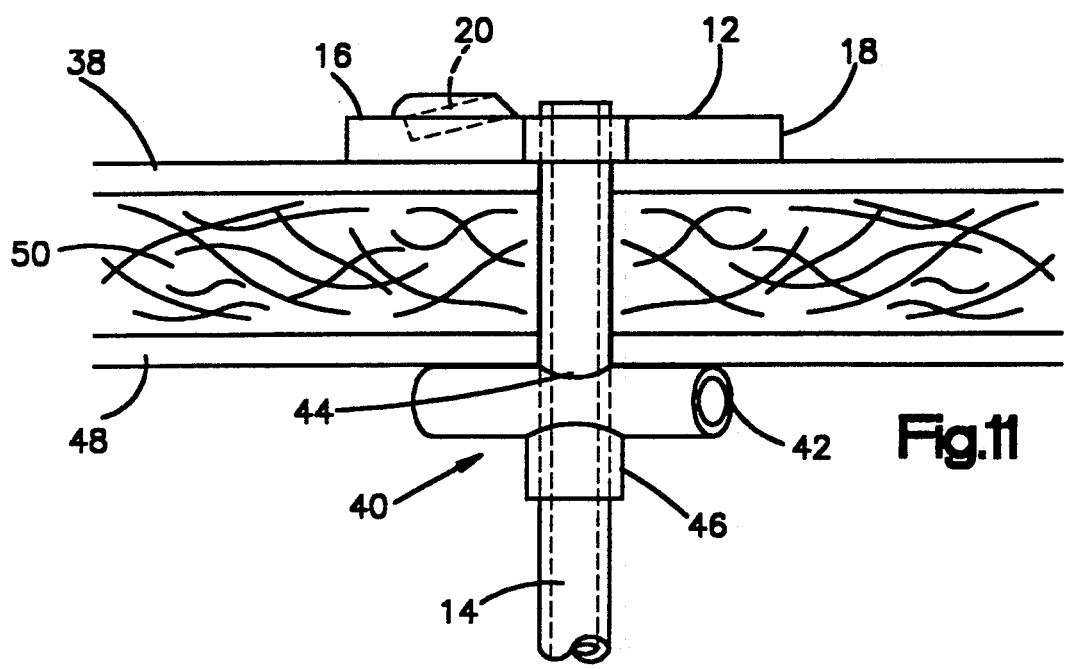
FIG. 11 is a side elevation view of the catheter according to the invention installed in a stoma and retained with a bolster.

FIG. 11 shows a bolster 40 consisting of a short length of resilient tubing 42 having a transverse hole 44 to accommodate the tube 14 and an elastic band 46 that may be expanded to slide along the tube 14 and allowed to contract to retain the tubing 42 against the outer wall 48.

Figure 12:
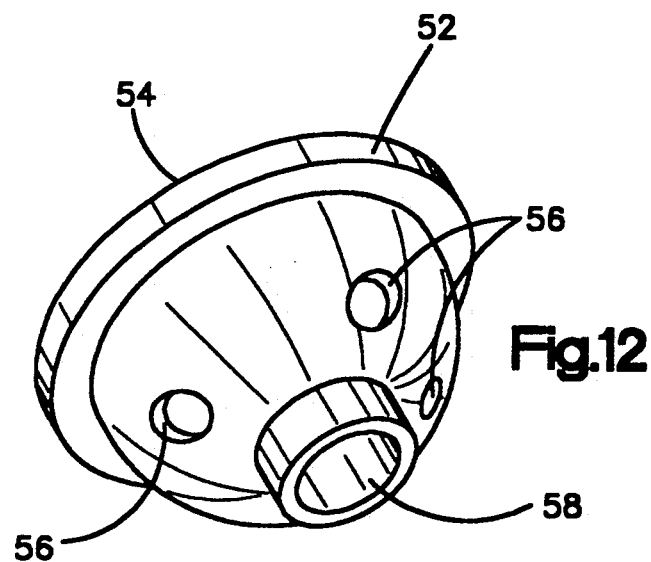
FIG. 12 is a perspective view of a bolster according to the invention.

FIGS. 9 and 12 show a new and improved bolster 52 for retaining the catheter 10. The bolster 52 is formed of a resilient material in a cup-shape having a mouth 54. Vent holes 56 are provided through the walls of the bolster 52, along with a central aperture 58. The aperture 58, is dimensioned to be expandable to slide over the tube 14 and to firmly grip the tube 14 when allowed to contract. Such expansion can be advantageously achieved by the use of a nasal speculum.

As shown in FIG. 9, the bolster 52 may be slid along the tube 14 and the mouth 54 moved into contact with the outer wall 48 and held there by the gripping action of the aperture 58.

Because the bolster 52 does not contact the mouth of the stoma 36, but instead of an area removed from the stoma 36, the bolster 52 allows air to enter the vent holes 56 and circulate about the entire periphery of the stoma 36. This exposure to air improves healing and decreases infection and irritation.

The embodiment of FIGS. 4 and 5 provides an alternate means for maintaining the catheter of the invention within the stoma. A resilient flange 60 is attached about the end of the tube 14' opposite the retainer 12'. The length of the tube 14' corresponds substantially to the length of the passage or stoma that will contain the catheter 10'.

In the preferred embodiment, the flange 60 consists of a pair of diametrically opposed substantially flat wings 62 and 64. A plug 66 may advantageously be provided at the end of a membrane 68 attached to the wing 62. The membrane 68 allows the plug 66 to be inserted into the inlet 70 of the catheter 10'. The plug 66 is dimensioned to seal the inlet 70 when inserted therein and may be removed as desired.

Once inserted in the stoma as described above, the catheter 10' is maintained within a stoma by trapping the wall about the stoma between the retainer 12' and the flange 60, similar to the case of the retainer and bolster combination shown in FIG. 11.

Figure 14:
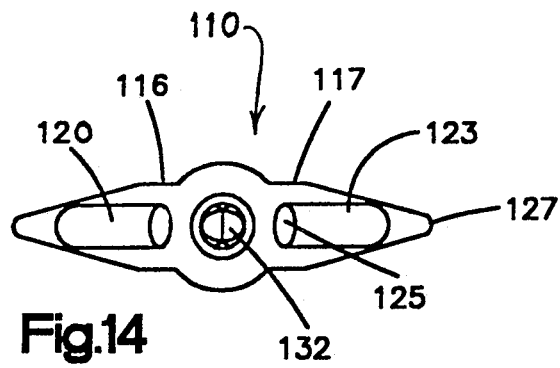
FIG. 14 is a top plan view of the embodiment of FIG. 13.
Figure 15:
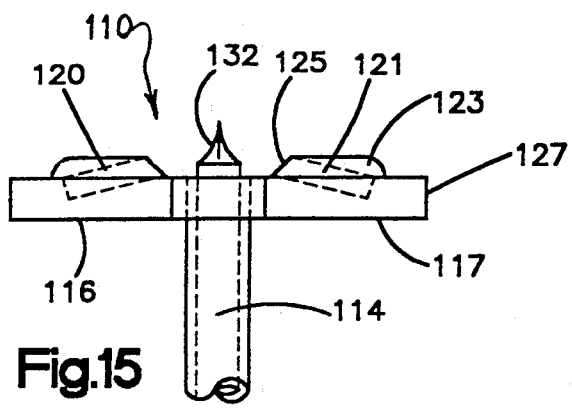
FIG. 15 is a side elevation view of the embodiment of FIG. 13.

Referring to FIGS. 14 and 15, a double-pocket embodiment of the invention is shown.

Similar to the embodiments of FIGS. 1, 2 and 6, the catheter has pocket 120. In addition, the diametrically opposed wing 117 is provided with a pocket 121, the top wall 123 of which protrudes above the general level of the wing 117. The mouth 125 of the pocket 121 is located toward the tube 114 on the top of the wing 117, while the pocket 121 extends within the wing 117 radially outward from the tube 114.

It would of course be possible to have the pockets on the bottom of the wings.

In the preferred embodiments, the wing 117 also tapers to a point 127.

As described previously, it is sometimes desirable to provide the catheter with a one-way valve, such as the duck-bill valve 132.

Figure 16:
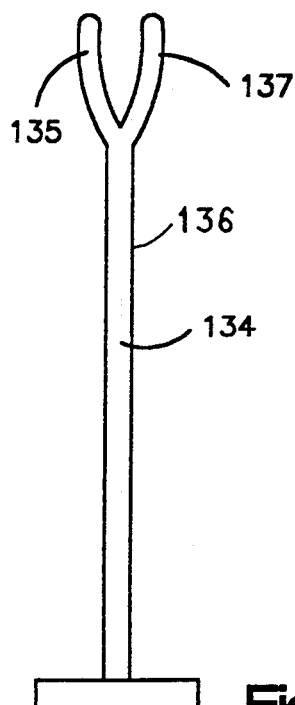
FIG. 16 is a side elevation view of the forked obturator.

Referring to FIG. 16, another type of obturator 134 is shown having a fork at one end of the rod 136 consisting of prongs 135 and 137.

While the double-pocket catheter 110 may be installed and removed as described previously for other embodiments of the invention, it may also be installed using the forked-obturator 134.

Figure 13:
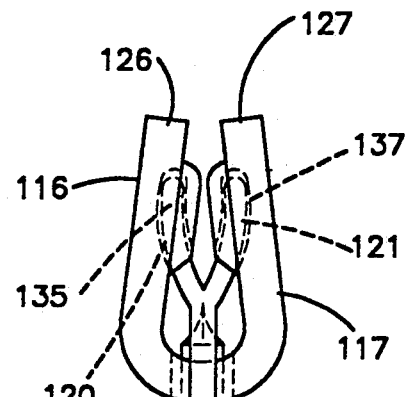
FIG. 13 is a perspective view of a double-pocket embodiment of the invention in its forked-obturator insertion configuration.

Referring to FIG. 13, the prongs 135, 137 may be inserted into the pockets 120 and 121 by folding the wings 116, 117 together beyond the end of the tube 114. The prongs 135, 137 then hold the wings 116, 117 in this folded-forward position.

When the rod 136 is oriented collaterally with the tube 114 with the prongs 135, 137 holding the wings 116, 117 in the folded-forward position, the folded wings/tube/obturator forms a small axial cross section assembly that may be inserted into a stoma, similar to that shown in FIG. 8. Once the wings 116, 117 are through the passage, the obturator 134 may be withdrawn, allowing the wings to return to their normal radial orientation.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. A catheter insertable into a passage through a wall using a rod having a tip, said catheter comprising:
   a resilient tube having a distal end, a central axis and a proximal end;
   a pair of resilient diametrically opposed, oppositely extending wings connected about the distal end; and
   a pocket in at least one of said wings, said pocket being spaced radially outward from the central axis of said tube and being adapted to receive the tip of the rod, whereby the pair of wings may be urged to a position collateral with the tube by inserting the tip in the pocket and orienting the rod collateral with the tube.

2. A catheter according to claim 1, wherein said pocket bearing wing tapers to a point.

3. A catheter according to claim 1, wherein said pocket extends radially outward within the pocket bearing wing.

4. A catheter according to claim 1, further comprising a one-way valve connected about the distal end, said valve being adapted to prevent a flow of fluid from said distal end to said proximal end.

5. A catheter according to claim 4, wherein said valve is a flapper valve.

6. A catheter according to claim 4, wherein said valve is a duck-bill valve.

7. A catheter according to claim 1, further comprising resilient flange means connected about the proximal end, the axial distance between the pair of wings and the flange means substantially corresponding to the length of said passage, whereby the wall may be retained about the tube between said pair of wings and said flange means.

8. A catheter according to claim 7, wherein said flange means comprises a pair of diametrically spaced, oppositely extending, substantially flat wings.

9. A catheter according to claim 8, further comprising a plug connected to the radially outer end of one of said wings by a flexible membrane which permits said plug to be inserted into the proximal end of the tube to close off the proximal end and removed therefrom as desired.

10. A catheter according to claim 1, further comprising a cupped resilient member having:
   a mouth;
   a central aperture, said aperture being expandable to slide onto the proximal end and along said tube and being contractible to grip said tube when released;
   and at least one vent hole between said aperture and said mouth, whereby the mouth of the member may be urged against the wall about the passage but spaced radially away therefrom and air may enter the vent hole and circulate within said member immediately adjacent said passage.

11. A bolster for retaining a catheter in a passage through a wall, said bolster comprising a cupped resilient member having:
   a mouth;
   a central aperture, said aperture being expandable to slide about said catheter and being contractible to grip said catheter when released;
   and at least one vent hole between said aperture and said mouth, whereby the mouth of the member may be urged against the wall about the passage but spaced radially away therefrom and air may enter the vent hole and circulate within said member immediately adjacent said passage.

12. A method for placement of a catheter into a passage using a rod having a tip, said catheter having a resilient tube having a proximal end and a distal end, a resilient retaining means connected about the distal end, and a pocket in said retaining means, said pocket being spaced radially outward from said tube and being adapted to receive the tip of the rod, the method comprising:
   inserting the tip of the rod into the pocket;
   orienting the rod collateral with the tube, thereby orienting the retaining means collateral with the tube; and
   inserting the retaining means along with a portion of the tube and rod into the passage.

13. A catheter insertable into a passage through a wall using a rod having a two-pronged forked tip, said catheter comprising:
   a resilient tube having a distal end and a proximal end;
   a resilient retaining means connected about the distal end; and
   a pair of pockets in said retaining means, said pockets being spaced radially outward in opposite directions from said tube and being adapted to receive said prongs, whereby said retaining means be urged to a folded position generally collateral with the tube and extending beyond the distal end by inserting the prongs in respective pockets and orienting the rod collateral with the tube.

14. A catheter according to claim 13, wherein said retaining means is substantially flat.

15. A catheter according to claim 14, wherein said retaining means comprises a pair of diametrically spaced, oppositely extending wings, each bearing one of said pockets.

16. A catheter according to claim 15, wherein said wings taper to a point.

17. A catheter according to claim 13, wherein said pockets extend radially outward within the retaining means.

18. A catheter according to claim 13, further comprising a one-way valve connected about the distal end, said valve being adapted to prevent a flow of fluid from said distal end to said proximal end.

19. A catheter according to claim 18, wherein said valve is a flapper valve.

20. A catheter according to claim 18, wherein said valve is a duck-bill valve.

21. A catheter according to claim 13, further comprising resilient flange means connected about the proximal end, the axial distance between the retaining means and the flange means substantially corresponding to the length of said passage, whereby the wall may be retained about the tube between said retaining means and said flange means.

22. A catheter according to claim 21, wherein said flange means comprises a pair of diametrically spaced, oppositely extending, substantially flat wings.

23. A catheter according to claim 22, further comprising a plug connected to the radially outer end of one of said wings by a flexible membrane which permits said plug to be inserted into the proximal end of the tube to close off the proximal end and removed therefrom as desired.

24. A catheter according to claim 13, further comprising a cupped resilient member having:
   a mouth;
   a central aperture, said aperture being expandable to slide onto the proximal end and along said tube and being contractible to grip said tube when released;
   and at least one vent hole between said aperture and said mouth, whereby the mouth of the member may be urged against the wall about the passage but spaced radially away therefrom and air may enter the vent hole and circulate within said member immediately adjacent said passage.

25. A method for placement of a catheter into a passage using a rod having a two-pronged forked tip, said catheter having a resilient tube having a proximal end and a distal end, a resilient retaining means connected about the distal end, and a pair of pockets in said retaining means, said pockets being spaced radially outward in opposite directions from said tube and being adapted to receive said prongs, the method comprising:
   inserting the prongs into respective pockets, thereby urging said retaining means to a folded position extending beyond the distal end;
   orienting the rod collateral with the tube, thereby orienting the retaining means collateral with the tube; and
   inserting the retaining means along with a portion of the tube and rod into the passage.

* * * * *